United States Patent [19]

Sakano et al.

[11] Patent Number: 5,541,090
[45] Date of Patent: Jul. 30, 1996

[54] PROCESS FOR PRODUCTION OF L-ASPARTIC ACID

[75] Inventors: Koichi Sakano, Ibaraki; Takaya Hayashi, Tsutiura; Masaharu Mukouyama, Ibaraki, all of Japan

[73] Assignee: Nippon Shokubai Co., Ltd., Osaka, Japan

[21] Appl. No.: 444,880

[22] Filed: May 19, 1995

[30] Foreign Application Priority Data

May 20, 1994 [JP] Japan .................................. 6-106927
Feb. 23, 1995 [JP] Japan .................................. 7-035285

[51] Int. Cl.$^6$ .......................................... C12P 13/20
[52] U.S. Cl. ........................... 435/109; 435/829; 435/849; 435/874
[58] Field of Search ..................... 435/109, 829, 435/874, 849

[56] References Cited

U.S. PATENT DOCUMENTS

| | | | |
|---|---|---|---|
| 3,391,059 | 7/1968 | Takamura et al. | 195/30 |
| 4,560,653 | 12/1985 | Sherwin et al. | 435/109 |
| 4,578,354 | 3/1986 | Cannon | 435/178 |
| 5,270,190 | 12/1993 | Nakayama et al. | 435/145 |
| 5,338,649 | 8/1994 | Inaba et al. | 430/430 |

FOREIGN PATENT DOCUMENTS

| | | |
|---|---|---|
| 0127940 | 12/1984 | European Pat. Off. . |
| 143183 | 12/1988 | Poland . |

OTHER PUBLICATIONS

Chemical Abstracts, vol. 79, No. 25, pp. 357–358, Dec. 24, 1973.
Chemical Abstracts, vol. 111, No. 15, p. 819, Oct. 9, 1989.

*Primary Examiner*—Herbert J. Lilling
*Attorney, Agent, or Firm*—Foley & Lardner

[57] ABSTRACT

A process for production of L-aspartic acid comprising the steps of (1) contacting (A) an enzyme-containing material having maleate isomerase activity and aspartase activity, or (B) an enzyme-containing product having maleate isomerase activity and an enzyme-containing material having aspartase activity, with a substrate solution containing maleic acid and ammonia, and/or ammonium maleate to form L-aspartic acid, and (2) recovering L-aspartic acid from the reaction solution, characterized by adding maleic anhydride and/or maleic acid to the reaction solution to crystallize L-aspartic acid, and (3) recycling the mother liquors as the substrate solution by addition of ammonia.

19 Claims, No Drawings

PROCESS FOR PRODUCTION OF L-ASPARTIC ACID

BACKGROUND OF THE INVENTION

1. Field of Invention

The present invention relates to a process for production of L-aspartic acid from maleic acid and ammonia characterized by recycling a reaction solution to prevent the discharge of waste water containing a large amount of ammonia, and to L-aspartic acid crystals accompanied with maleic acid and/or salt thereof.

2. Related Art

Various processes for production of L-aspartic acid from ammonium fumarate using microorganisms having aspartase activity are known. For example, there are a process wherein a microorganism resistant against α-aminobutylic acid is cultured and the cultured cells are used for the reaction (Japanese Examined Patent Publication No. 61-29718), a process using microbial cells cultured in a fumaric acid-containing medium (Japanese Laid-Open Patent Publication No. 60-120983), a process using a column filled with *Escherichia coli* immobilized in natural polysaccharides (Japanese Laid-Open Patent Publication No. 53-6483), or the like.

Various advanced processes using aspartase or microorganisms having aspartase activity have been developed, but fumaric acid which is more expensive than maleic acid is used as the substrate, so that the costs of raw materials are still high.

The L-aspartic acid is usually recovered by precipitation of L-aspartic acid crystals by addition of a mineral acid such as sulfuric acid to the reaction solution, and separation of the crystals. In this case, a large amount of byproduct such as ammonium sulfate is generated. Thus, for economical and environmental reasons, a process -wherein L-aspartic acid is precipitated and the mother liquors are recycled in a closed system is very desirable.

U.S. Pat. No. 4560653 discloses a process for production of L-aspartic acid wherein aspartase or aspartase-producing microorganism is reacted with fumaric acid and ammonia, and L-aspartic acid is precipitated by addition of maleic acid and filtrated from the solution and the mother liquors are recycled. However, to convert maleic acid in the mother liquors to fumaric acid, the reaction solution is heated with a chemical catalyst such as bromide. Accordingly this is obviously a troublesome process containing removal of the chemical catalyst and the trace color bodies prior to recycle of mother liquors.

SUMMARY OF INVENTION

The present invention is intended to provide a simple process for production of L-aspartic acid using cheap starting substrates and not discharging waste water containing a large amount of ammonium salt.

In the present invention, L-aspartic acid is directly produced from maleic acid by enzymes or microorganisms and the mother liquors are recycled after recovering L-aspartic acid from the reaction solution.

The present invention provides a process for production of L-aspartic acid comprising the steps of (1) contacting (A) an enzyme-containing material having maleate isomerase activity and aspartase activity, or (B) an enzyme-containing material having maleate isomerase activity and an enzyme-containing material having aspartase activity with a substrate solution containing maleic acid and ammonia, and/or ammonium maleate to form L-aspartic acid, and (2) recovering L-aspartic acid from the reaction solution, characterized by adding maleic anhydride and/or maleic acid to the reaction solution to crystallize L-aspartic acid, and (3) recycling the mother liquors as the substrate solution by addition of ammonia.

The present invention also provides an industrially useful L-aspartic acid product containing maleic acid.

According to the present invention, maleic acid cheaper than fumaric acid is used to produce L-aspartic acid, and the mother liquors are recycled as the substrate solution without addition of chemical catalyst such as bromide. Therefore, L-aspartic acid can be produced cheaply and efficiently.

DETAILED DESCRIPTION

According to the present invention, any microorganism having maleate isomerase activity and aspartase activity can be used, and the genus Alcaligenes such as *Alcaligenes faeculis* ATCC 8750 are preferably used.

In addition, a combination of a microorganism having maleate isomerase activity and a microorganism having aspartase activity can be used.

Example of Microorganism having maleate isomerase activity which converts maleic acid to fumaric acid include the genus Pseudomonas such as *Pseudomonas maltohilia* ATCC 13270.

Example of Microorganism having aspartase activity which convert fumaric acid to L-aspartic acid include the genus Escherichia such as *Escherichia coli* ATCC 11303, ATCC 9637 and ATCC 27325, and microorganism belonging to the genus Brevibacterium.

A microorganism having maleate isomerase activity and a microorganism having aspartase activity can be used as a mixture or separately for reactions.

Any convenctional media can be used, for cultivation of the cells of the above-mentioned microorganisms. Sugars such as glucose, fructose, sucrose etc., organic acids such as maleic acid, fumaric acid, malic acid, acetic acid etc., as well as alcohols such as ethanol may be used as carbon source of the medium.

Ammonia, ammonium salts such as ammonium sulfate, ammonium chloride, ammonium nitrate etc. may be used as nitrogen source. In addition, pepton, yeast extract, corn steep liquor, casamino acids etc. may be also used as nitrogen sources. As inorganic salts, potassium monohydrogen phosphate, potassium dihydrogen phosphate, magnesium phosphate, ferrous phosphate etc. may be used. In addition, vitamins may be optionally added.

Cultivation is carried out under an aerobic condition provided by aeration, agitation, shaking etc. at 20° C. to 40° C., preferably 28° to 37° C. A pH of a culture medium is from 5 to 10, preferably 7 to 8. Adjustment of pH is carried out by addition of an acid or alkaline solution. A concentration of the carbon source at the onset of culturing is from 0.05 to 10%, preferably 0.5 to 2%. Cultivation time is from 10 hours to 4 days, preferably 15 hours to 3 days.

The microbial cells obtained by culturing as described above are collected by centrifugation or filtration, washed with water or a buffer solution or a physiological saline solution, and used for the reaction. The enzyme-containing material used for the reaction may be microbial cells, disrupted cells physically or chemically treated for example by ultrasonication, grinding, freezing/thawing, surfactant treatment, and purified enzymes obtained by conventional procedures such as salting out with ammonium sulfate, acetone precipitation.

In addition, the above-mentioned microbial cells or disrupted cells, or enzymes may be immobilized in or on a carrier. Examples of carrier are natural polymers such as cellulose, alginic acid, K-carrageenan etc., or synthetic polymers such as ion exchange resin, polyacrylamide etc. By immobilization of the enzymes or the microbial cells, separation of the reaction solution from the enzyme-containing material becomes easy and recycle of the mother liquors recovered from the reaction solution is easily carried out.

Reaction may be carried out after enzymes which interfere the reaction for L-aspartic acid production are inactivated. For example, the enzyme-containing material may be heated to about 40° C. to 60° C. in the presence of L-aspartic acid and ammonium ion to inactivate fumarase.

Carboxylic acid used as the substrate in the present invention is at least one of maleic anhydride, maleic acid or salts of maleic acid. Ammonia used in the present invention may be gaseous ammonia or aqueous ammonia solution which is preferable due to easy handling. Concentration of aqueous ammonia solution is not particularly limited, and a concentration of 10 to 35% is preferably used from an industrial point of view.

An amount of ammonia added to the reaction solution is preferably at least 1.0 time and at most 3.0 times an amount of maleic acid contained in the reaction solution. When an amount of ammonia is less than one time an amount of maleic acid, yield of L-aspartic acid is low, and when an amount of ammonia is much more than three times an amount of maleic acid, biocatalysts participating in the reaction may become possibly unstable. In addition, alkaline metal hydroxide such as sodium hydroxide or potassium hydroxide may be added within the above-mentioned amount of ammonia.

A pH of the substrate solution is from 5 to 10, preferably 7.0 to 9.0, and more preferably 8.0 to 9.0. When maleic acid and ammonia are mixed, the mixing can be carried out in any manner, and preferably one component is preferably gradually added to a total amount of another component, rather than total amounts of both the components are mixed at once. Especially it is preferable that ammonia is gradually added to an aqueous solution of maleic acid.

A substrate solution containing maleic acid and ammonia is prepared with water or a buffer. As a buffer solution, conventional buffer solution such as phosphate buffer may be used. The concentration of maleic acid is from 5 to 40%, preferably 10 to 30%, and more preferably 10 to 25% in view of solubility of maleate and reactivity of the biocatalyst.

To the substrate solution preferably may be added a metal salt such as manganese salt, magnesium salt, zinc salt, calcium salt, nickel salt, cobalt salt, iron salt etc., in a concentration of 0.1 to 50 mM, preferably 1 to 10 mM. In addition, an SH group-containing substance such as mercaptoethanol, glutathione, cysteine, dithiothreitol may be preferably added in a concentration of 0.1 to 50 mM, and preferably 1 to 10 mM.

The shape of reactor in the present invention is not particularly limited, and any known reactor such as buckettype reactor, column-type reactor etc. can be used. A single reactor or plural reactors may be used. In case of column-type reactor, flow rate can be changed dependent on the kind of enzyme-containing product filled in the column.

Reaction temperature is 20° to 50° C., preferably 25° to 40° C.

After reaction of maleic acid and ammonia under the conditions as described above, maleic anhydride and/or maleic acid is added to the resulting reaction solution to crystallize L-aspartic acid. In addition, salts of maleic acid can be added in an extent that does not interfere recycling the mother liquors. As a salt of maleic acid, ammonium maleate, sodium maleate, potassium maleate etc. can be used.

The recycle of the mother liquors becomes possible by addition of maleic acid to crystallize L-aspartic acid. If mineral acid is used to crystallize L-aspartic acid, ammonium salt of the mineral acid accumulates, and therefore a desalting operation is necessary for the recycle the mother liquors. Accordingly the addition of mineral acid is not preferable. Here, maleic acid added to crystallize L-aspartic acid includes maleic anhydride, maleic acid or salts thereof. Moreover maleic acid can be added as an aqueous solution or slurry. In this case a concentration of a maleic acid aqueous solution is preferably at least 20% by weight for easy operation.

An amount of maleic acid added to a reaction solution to crystallize L-aspartic acid depends on an amount of L-aspartic acid (present as a salt) contained in the solution. Molar ratio of maleic acid against L-aspartic acid in the solution is preferably from 0.5 to 1.5, more preferably 0.8 to 1.2, and more preferably 1.005 to 1.1. If an less amount of maleic acid is added, yield of L-aspartic acid recovered as the crystals becomes lower, while an excess amount of maleic acid is added, chemicals other than L-aspartic acid may possibly crystallize.

Maleic acid is preferably gradually added to a reaction solution to crystallize L-aspartic acid. According to this method, size of crystals of L-aspartic acid are large and therefore the method is suitable for separation of the crystals from the solution. Crystallization of L-aspartic acid is carried out at 0° to 100° C. for 10 minutes to 4 hours, preferably at 20° to 80° C. for 30 to 120 minutes.

Without heating an reaction solution, for example, maleic acid may be added at 20° C. to 50° C. which is a reaction temperature and the mixture is agitated for 30 to 120 minutes to crystallize and recover L-aspartic acid in high yield. Crystallization of L-aspartic acid at 20° C. to 50° C. is highly preferred from an industrial point of view, because L-aspartic acid can be crystallized and recovered without heating and cooling the reaction solution.

The L-aspartic acid crystals are separated by a conventional method such as centrifugation, filtration etc. The crystals are washed according to conventional procedures. The crude crystals of the L-aspartic acid contain about 7 to 15% by weight of maleic acid or salts thereof, and the content of maleic acid and/or salts thereof can be decreased by washing.

For example, one washing operation with water reduces the content of maleic acid and/or salts thereof to about 1% by weight, and an additional washing with water reduces the content of maleic acid and/or salts thereof to about 0.03% by weight. Further repeated washing with water can reduce the content of maleic acid and/or salts thereof to about 0.01% by weight. However, considering the recycle of the mother liquors as the substrate solution, the use of a large amount of water for washing is not preferable. Note that a washing water may be mixed with the mother liquors from which L-aspartic acid crystals has been separated, and the solution may be re-used. In this case, the washing water may be concentrated prior to the mixing with the mother liquors.

In this way, L-aspartic acid crystals accompanied with 0.01 to 15% by weight and preferably 0.01 to 1% by weight of maleic acid and/or salts thereof can be very easily produced, and an average size of the crystals can be controlled by changing conditions for crystallization. Crystals having average particle size of 50 to 500 μm can be obtained, which have good properties for handling. This L-aspartic acid product is useful as for industrial use, for example, a starting material for surfactants, metal ion sequenstrant, detergent composition, cosmetic composition, anti-corrosive agent, pharmaceuticals, coatings, and the like. In addition, it is useful as starting material for the production of industrially useful polymers such as poly(aspartic acid) and derivatives thereof. The L-aspartic acid product may be also used as a food additive by further purification.

The mother liquors from which L-aspartic acid have been separated are used as the substrate solution for further production of L-aspartic acid. In addition, a washing water derived from the washing of crude L-aspartic acid crystals can be mixed with the mother liquors for re-using. Maleic acid, ammonia, water etc. may be added to the mother liquors (possibly including washing water) to adjust a maleic acid concentration in the mother liquors to the initial concentration for previous reaction, to adjust the molar ratio of ammonia to maleic acid to about 1 to 3 mole equivalents, and to adjust the volume of recycled mother liquors to that of the previous substrate solution. The cycles comprising (1) reaction of maleic acid and ammonia with microbial cells or disrupted cells (2) crystallization of L-aspartic acid (3) separation and washing of L-aspartic acid (4) recycle of the mother liquors are repeated. The mother liquors can be recycled at least 10 times.

The addition of ammonia to the mother liquors is preferably carried out considering the following points to maintain the enzyme activities of microbial cells or disrupted cells or enzymes as long as possible. Namely, ammonia is added to the mother liquors so that an amount of ammonia in the recycled mother liquid is 1 to 3 mole equivalent, preferably 1.5 to 2.5 mole equivalent relating to an amount of maleic acid in the mother liquors.

According to the present invention a substrate solution containing maleic acid and ammonia, or ammonium maleate wherein molar ratio of ammonia to maleic acid is from 1 to 3 is contacted with microbial cells having both the maleate isomerase activity and aspartase activity, or with microbial cells having maleate isomerase activity and microbial cells having aspartase activity, or alternatively disrupted cells or enzymes thereof at 20° to 50° C.

An enzyme-containing material such as microbial cells having maleate isomerase activity and an enzyme-containing material having aspartase activity may be used as a mixture. Alternatively, maleate isomerase-containing material may first convert maleic acid to fumaric acid, and then aspartase-containing product may convert the fumaric acid to L-aspartic acid. All or a part of enzyme-containing materials such as microbial cells or disrupted cells can be replaced with corresponding fresh one, when the activity of the prior-used enzyme-containing material decreases.

Ammonium L-aspartate is formed after the reaction and maleic anhydride, maleic acid or salt of maleic acid is added to the resulting reaction solution to crystallize L-aspartic acid. The L-aspartic acid crystals are separated from the solution. The recovered crystals are washed with water to reduce an amount of maleic acid and/or salt thereof. L-aspartic acid produced in this manner is highly useful for the industrial material.

The mother liquors from which the crystals have been removed, together with washing water, are recycled and re-used as a substrate solution for the production of L-aspartic acid. By this manner, cheap raw materials are efficiently used, and an amount of waste water containing a large amount of ammonia salts is remarkably decreased.

EXAMPLES

The present invention is explained in detail by the following Examples, though the scope of the present invention should not be limited thereon. Note that reaction products were analyzed by liquid chromatography.

Example 1

*Alcaligenes faecalis* ATCC 8750 was inoculated into a 10 L jar fermentor containing a medium (6 L) (pH 6.5) composed of maleic acid (1 wt %), malonic acid (0.5 wt %), ammonium sulfate (0.5 wt %), potassium monohydrogen phosphate (0.3 wt %), potassium dihydrogen phosphate (0.1 wt %), magnesium sulfate.7 hydride (0.05 wt %), and yeast e wtxtract (2 wt %). Cultivation was carried out at 30° C. for 20 hours with aeration and agitation, and the cultured cells were collected by centrifugation.

A substrate solution was prepared as follow. 470 g of 25 wt % aqueous ammonia solution (molar ratio to maleic acid was about 2.0) was added into 400 g of maleic acid dissolved in deionized water, to prepare 2 L of ammonium maleate (pH 8.4). To the resulting ammonium maleate aqueous solution were added 2 g Triton X-100, 0.4 g magnesium sulfate, and 1.56 g β-mercaptoethanol. The collected *Alcaligenes faecalis* cells were added to the substrate solution, which was then gently stirred at 30° C. for 24 hours.

After the reaction, ammonium L-aspartate was formed with a molar yield of 99.0% based on maleic acid. The reaction solution from which the cells were removed was warmed at about 70° to 80° C., while 410 g maleic acid was added to the reaction solution, and then the mixture was cooled to 30° C. At this time, pH of the solution was 3.7. The crystals of L-aspartic acid were separated by filtration, so as to recover 1.6 L of mother liquors. The crude crystals were 510 g (excluding water) (88.4 wt % aspartic acid, 11.0 wt % maleic acid, 400 μm average crystal size). The crystals were washed with 300 ml of water and dried so as to obtain 450 g crystals (99.0 wt % aspartic acid, 0.58 wt % maleic acid, 150 μm average crystal size).

The mother liquors and the wash water were combined, concentrated under a reduced pressure, and 25 wt % aqueous ammonia solution was added to the concentrate to adjust pH to 8.4. Deionized water was added to the concentrate to bring the volume to 2 L. This solution was used as a substrate solution. To this solution were added the cells recovered by centrifugation as described above, and the reaction was carried out under the same conditions as described above. After the reaction, ammonium L-aspartate was formed in a molar yield of 99.2% based on maleic acid.

After removing the cells from the reaction solution by centrifugation, 410 g of maleic acid was added to the solution, and the operations of heating and cooling were carried out as described above. Crystals of L-aspartic acid were filtered with suction, washed twice with about 300 ml of water, filtered with suction, and after thoroughly removing water, dried to obtain 460 g of L-aspartic acid crystals. The purity of the crystals was 99.6 wt % (0.02 wt % content of maleic acid; 80 μm average crystal size).

The crystals were washed with 2 L of water, filtered with suction, and dried to obtain L-aspartic acid crystals with purify of 99.6 wt % (0.01 wt % content of maleic acid; 80 μm average crystal size).

Example 2

According to the same procedure of Example 1, cells of *Alcaligenes faecalis* ATCC 8750 was added to 2 L of an ammonium maleate substrate solution containing 400 g of maleic acid, and the substrate solution was gently stirred at 30° C. for 24 hours. After the reaction, ammonium L-aspartate was formed with a molar yield of 99.0% based on maleic acid. To the reaction solution from which the cells had been removed by centrifugation, was added 410 g of maleic acid at 30° C., to precipitate crystals of L-aspartic acid. After the addition, a temperature of the solution was 34.5° C., and pH value thereof was 3.8. L-aspartic acid crystals were separated by filtration, so as to recover 1.6 L of mother liquors. The crude crystals was 502 g (Excluding water) (89.1 wt % aspartic acid, 10.2 wt % malic acid, 250 μm average crystal size). The crystals were washed with 300 ml of water and dried so as to obtain 447 g of L-aspartic acid crystals (99.0 wt % aspartic acid, 0.62 wt % maleic acid, 100 μm average crystal size).

The mother liquors and the wash water were concentrated under a reduced pressure, and 25 wt % aqueous ammonia solution was added to the concentrate to adjust pH to 8.4. Deionized water was added to the solution to bring the volume to 2 L. This solution was used as a substrate solution. To this solution were added the cells recovered by centrifugation as described above, and the reaction was carried out under the same conditions as described above. After the reaction, ammonium L-aspartate was formed in a molar yield of 99.3% based on maleic acid.

The reaction solution was centrifuged to eliminate the cells, 410 g of maleic acid was added to the reaction solution as described above, and the operations of crystallization and recovery were carried out as described above. L-aspartic acid crystals were washed twice with about 300 ml of water, and dried to obtain 455 g (excluding water) of L-aspartic acid crystals. The purity of the crystals was 99.4 wt %, and an average crystal size was 60 μm.

Example 3

According to the same procedure of Example 1, cells of *Alcaligenes faecalis* ATCC 8750 was added to 2 L of an ammonium maleate substrate solution containing 400 g of maleic acid, and the substrate solution was gently stirred at 30° C. for 24 hours. After the reaction, ammonium L-aspartate was formed with a molar yield of 99.0% based on maleic acid. To the reaction solution from which the cells had been removed by centrifugation, was added 1.23 kg of 33.3 wt % maleic acid aqueous solution at 30° C. After the addition, a temperature of the solution was 38.5° C., and pH value of thereof was 3.7. L-aspartic acid crystals were separated by filtration, so as to recover 2.37 L of mother liquors. The crude crystals were 481 g (excluding water) (93.6 wt % aspartic acid, 6.0 wt % maleic acid, 250 μm average crystal size). The crystals were washed with about 300 ml of water and dried so as to obtain 448 g (excluding water) of L-aspartic acid crystals (99.1 wt % aspartic acid weight, 0.50 wt % maleic acid, 200 μm average crystal size).

The mother liquors 2.37 L and the wash water were combined and concentrated under a reduced pressure to 1.7 L, and 240 g of 25 wt % aqueous ammonia solution was added to the concentrate to adjust pH to 8.4. Deionized water was added to the solution to bring the volume to 2 L. This solution was used as a substrate solution. To this solution were added the cells recovered by centrifugation as described above, and the reaction was carried out under the same conditions as described above. After the reaction, ammonium L-aspartate was formed in molar yield of 99.3% based on maleic acid.

The reaction solution was centrifuged to eliminate the cells, and 1.23 kg of 33.3 wt % by weight maleic acid aqueous solution was added to the reaction solution to crystallize L-aspartic acid. L-aspartic acid crystals were filtered with suction, washed twice with about 300 ml of water, and dried to obtain 460 g (excluding water) of L-aspartic acid crystals. The purity of the crystals was 99.3 wt % (content of maleic acid 0.44 wt %) (average crystal size was 200 μm).

Example 4

According to the same procedures of Example 1, 200 g maleic acid was dissolved in deionized water, and 235 g of 25 wt % aqueous ammonia solution was added thereon. The cells of *Alcaligenes faecalis* ATCC 8750 was added to 2 L of an ammonium maleate substrate solution containing 200 g maleic acid, and the substrate solution was gently stirred at 30° C. for 24 hours. After the reaction, ammonium L-aspartate was formed with a molar yield of 99.0% based on maleic acid. To the reaction solution from which the cells had been removed by centrifugation, was added 205 g maleic acid at 30° C. After the addition, a temperature of the solution was 32.5° C., and pH thereof was 3.7. L-aspartic acid crystals were separated by filtration, so as to recover 1.75 L of mother liquors. On the other hand, the amount of the filtrated crude crystals of L-aspartic acid was 245 g (excluding water) (91.4 wt % aspartic acid, 8.0 wt % maleic acid, 300 μm average crystal size). The crystals were washed with about 300 ml of water and dried so as to obtain 225 g of L-aspartic acid crystals (99.0 wt % aspartic acid, 0.69 wt % maleic acid, 150 μm average crystal size).

The mother liquors and the wash water were concentrated under a reduced pressure, and 25 wt % aqueous ammonia solution was added to the concentrate to adjust pH value to 8.4. Deionized water was added to the solution to bring the volume to 2 L. This solution was used as a substrate solution. To this solution were added the cells recovered by centrifugation as described above, and the reaction was carried out under the same conditions as described above. After the reaction ammonium L-aspartate was formed in a molar yield of 98.9% based on maleic acid.

The reaction solution was centrifuged to eliminate the cells, and 205 g of maleic acid was added to the reaction solution as described above, and the operations of crystallization and recovery of L-aspartic acid were carried out as described above. L-aspartic acid crystals were washed twice with about 300 ml of water, and dried to obtain 228 g (excluding water) of L-aspartic acid crystals. The purity of the crystals was 99.5 wt % and average crystal size was 80 μm.

Example 5

According to the same procedure of Example 1, 600 g maleic acid was dissolved in deionized water, and 705 g of 25 wt % aqueous ammonia solution (molar ratio to maleic acid was about 2.0) was added thereon. The cells of *Alcaligenes faecalis* ATCC 8750 were added to 2 L of an ammonium maleate substrate solution (pH 8.4) containing 600 g maleic acid, and the substrate solution were gently stirred at 30° C. for 72 hours. After the reaction, ammonium L-aspartate was formed with a molar yield of 98.8% based on maleic acid. To the reaction solution from which the cells had been removed by centrifugation, was added 610 g maleic acid at 30° C. After the addition, a temperature of the solution was 37.0° C., and pH value thereof was 3.8.

L-aspartic acid crystals were separated by filtration, so as to recover 1.5 L of mother liquors. The crude crystals was 769 g (excluding water) (88.0 wt % aspartic acid, 11.4 wt % maleic acid, 250 μm average crystal size). The crystals were washed with about 600 ml of water and dried so as to obtain 675 g of L-aspartic acid crystals (98.8 wt % aspartic acid, 0.77 wt % maleic acid, 100 μm average crystal size).

The mother liquors and the wash water were concentrated under a reduced pressure, and 25 wt % aqueous ammonia solution was added to the concentrate to adjust pH to 8.4. Deionized water was added to the concentrate to bring the volume to 2 L. This solution was used as a substrate solution. Namely, to this solution were added the cells recovered by centrifugation as described above, and the reaction was carried out under the same conditions as described above. After the reaction the reaction solution contained ammonium L-aspartate was formed in a molar yield of 98.8% based on maleic acid.

The reaction solution was centrifuged to eliminate the cells, 610 g of maleic acid was added to the reaction solution as described above, and operations of crystallization and recovery of L-aspartic acid were carried out as described above. L-aspartic acid crystals were washed twice with about 1 L water, and dried to obtain 673 g (excluding water) of L-aspartic acid. The purity of the crystals was 99.5 wt %, and average crystal size was 150 μm.

Example 6

*Pseudomonas maltophilia* ATCC 13275 was inoculated into a 10 L jar fermentor containing a medium (6 L) (pH 6.5) composed of maleic acid (1 wt %), ammonium sulfate (0.5 wt %), potassium monohydrogen phosphate (0.3 wt %), potassium dihydrogen phosphate (0.1 wt %), magnesium sulfate.7 hydride (0.05 wt %), and yeast extract (2 wt %). Cultivation was carried out at 30° C. for 20 hours with aeration and agitation, and the resulting cultured cells were collected by centrifugation.

On the other hand, *Escherichia coli* ATCC 11303 was inoculated into a 2 L jar fermentor containing a medium (1 L) (pH 7.5) composed of fumaric acid (2%), corn steep liquor (2%), yeast extract (2%), monopotassium phosphate (0.1%), and magnesium sulfate.7 hydride (0.05%). Cultivation was carried out at 37° C. with aeration and agitation for 20 hours, and the resulting cultured cells were recovered by centrifugation.

470 g of 25 wt % aqueous ammonia solution (molar ratio to maleic acid was about 2) was added into 400 g of maleic acid dissolved in deionized water, to prepare 2 L of ammonium maleate (pH 8.4). To the resulting ammonium maleate aqueous solution were added 2 g Triton X-100, 0.4 g magnesium sulfate, and 1.56 g β-mercaptoethanol. The collected *Pseudomonas maltophilia* cells and the collected *Escherichia coli* cells were added to the substrate solution, which was then gently stirred at 30° C. for 24 hours.

After the reaction, ammonium L-aspartate was formed with a molar yield of 99.3% based on maleic acid. The reaction solution from which the cells were removed was warmed to 70° to 80° C., while 410 g maleic acid was added to the reaction solution, and then the mixture was cooled to 30° C. to precipitate crystals of L-aspartic acid. At this time, pH of the solution was 3.8. The crystals were separated by filtration, so as to recover 1.70 L of mother liquors. The crude crystals were 505 g (excluding water) (90.0 wt % aspartic acid, 9.5 wt % maleic acid, 350 μm average crystal size). The crystals were washed with about 300 ml of water and dried so as to obtain 451 g crystals (99.1 wt % aspartic acid, 0.55 wt % maleic acid, 100 μm average crystal size).

The mother liquors and the wash water were combined, concentrated under a reduced pressure, and 25 wt % aqueous ammonia solution was added to the concentrate to adjust pH to 8.4. Deionized water was added to the concentrate to bring the volume to 2 L. This solution was used as a substrate solution. To this solution were added the cells recovered by centrifugation as described above, and the reaction was carried out under the same condition as described above. After the reaction, ammonium L-aspartate was formed in a molar yield of 99.5% based on maleic acid.

After removing the cells from the reaction solution by centrifugation 410 g of maleic acid was added to the solution, and the operations of washing and drying were carried out as described above to obtain 455 g (excluding water) of crystals of L-aspartic acid. The purity of the crystals was 99.0 wt % (content of maleic acid 0.6 wt %; 100 μm average crystal size).

The mother liquors and the wash water were recycled and re-used as the substrate solution, to repeat the above-mentioned procedures 10 times (the mother liquors were recycled 9 times) using the fresh cells of the above-mentioned two microorganisms for each reaction. The molar yield of L-aspartic acid obtained in the 10th cycle was 95.0% based on maleic acid added in the 9th cycle. The purity of L-aspartic acid was 99.3 wt %, content of maleic acid was 0.52 wt % and average crystal size was 100 μm.

Example 7

According to the same procedure of Example 6, the cells of *Pseudomonas maltophilia* ATCC 13270 and the cells of *Escherichia coli* ATCC 11303 were added to 2 L of an ammonium maleate substrate solution containing 400 g of maleic acid, and the substrate solution was gently stirred at 30° C. for 24 hours. After the reaction, ammonium L-aspartate was formed with a molar yield of 99.3% based on maleic acid. To the reaction solution from which the cells had been removed by centrifugation was added 410 g maleic acid at 30° C. After the addition, a temperature of the solution was 34° C., and pH valve thereof was 3.7. L-aspartic acid crystals were separated by filtration so as to recover 1.6 L of mother liquors. The crude crystals were 517 g (excluding water) (88.0 wt % aspartic acid, 10.7 wt % maleic acid, 400 μm average crystal size). The crystals were washed with about 400 ml of water and dried so as to obtain 452 g (excluding water) of L-aspartic acid crystals (98.6 wt % aspartic acid, 1.0 wt % maleic acid, 300 μm average crystal size).

The mother liquors and the wash water were concentrated under a reduced pressure, and 25 wt % aqueous ammonia solution was added to the concentrate to adjust pH to 8.4. Deionized water was added to the concentrate to bring the volume to 2 L. This solution was used as a substrate solution. To this solution were added the cells recovered by centrifugation as described above, and the reaction was carried out under the same conditions as described above. After the reaction, ammonium L-aspartate was formed in a molar yield of 98.5% based on maleic acid.

The reaction solution was centrifuged to eliminate the cells, 410 g maleic acid was added to the reaction solution as described above, and the operations of crystallization and recovery were carried out as described above. L-aspartic acid crystals were washed twice with about 300 ml water, and dried to obtain 457 g (excluding water) of L-aspartic acid crystals. The purity of L-aspartic acid thus obtained was 99.5 wt %, and average crystal size was 100 μm.

We claim:

1. A process for production of L-aspartic acid comprising the steps of (1) contacting (A) an enzyme-containing material having maleate isomerase activity and aspartase activity, or (B) an enzyme-containing material having maleate isomerase activity and an enzyme-containing material having aspartase activity, with a substrate solution containing maleic acid and ammonia, and/or ammonium maleate to form L-aspartic acid, and (2) recovering L-aspartic acid from the reaction solution, characterized by adding maleic anhydride and/or maleic acid to the reaction solution to crystallize L-aspartic acid, and (3) recycling the mother liquors as the substrate solution by addition of ammonia.

2. A process according to claim 1, wherein ammonia is added to the mother liquors so that an amount of ammonia is from 1.0 to 3.0 mole equivalent relating to maleic acid contained in the mother liquors, and then the mother liquors are recycled as the substrate solution.

3. A process according to claim 1, wherein the mother liquors are recycled as the substrate media after adjusting the pH to 5 to 10.

4. A process according to claim 1, wherein the enzyme-containing material having maleate isomerase activity and aspartase activity, the enzyme-containing material having maleate isomerase activity, and/or the enzyme-containing material having aspartase activity are microbial cells, disrupted cells or enzymes, or immobilized material containing the same.

5. A process according to claim 1, wherein an amount of maleic anhydride, and/or maleic acid added to the reaction solution is from 0.5 to 1.5 mole equivalent relating to an amount of L-aspartic acid present in the reaction solution.

6. A process according to claim 5, wherein an amount of maleic anhydride and/or maleic acid is 1.005 to 1.5 mole equivalent relating to an amount of L-aspartic acid contained in the reaction solution.

7. A process according to claim 1, wherein the maleic anhydride and/or maleic acid are added to the reaction solution at a temperature of 20° to 50° C.

8. A process according to claim 1, wherein the maleic anhydride and/or maleic acid are added to the reaction solution without heating the reaction solution.

9. A process according to claim 1, wherein L-aspartic acid crystals recovered by addition of maleic anhydride and/or maleic acid are washed with water, and the wash water is mixed with the mother liquors from which L-aspartic acid has been removed, and the mixture is recycled as the substrate solution.

10. A process according to claim 1, wherein L-aspartic acid crystals accompanied with 0.01 to 15% by weight of maleic acid and/or a salt thereof are obtained as the final product.

11. A process according to claim 10, wherein L-aspartic acid crystals accompanied with 0.01 to 1% by weight of maleic acid and/or a salt thereof and having an average size of 50 to 500 μm are obtained as the final product.

12. L-aspartic acid crystals according to claim 1, wherein the maleic anhydride and/or maleic acid are added to the reaction solution without heating the reaction solution.

13. L-aspartic acid crystals accompanied with 0.01 to 1% by weight of maleic acid and/or salt thereof, and having an average size of 50 to 500 μm.

14. L-aspartic acid crystals having an average size of 50 to 500 μm and comprising 0.01 to 16 by weight of maleic acid and/or a salt thereof, said crystals produced by a process comprising:

(1) contacting (A) an enzyme containing material having maleate isomerase activity and aspartase activity, or (B) an enzyme-containing material having maleate isomerase activity and an enzyme-containing material having aspartase activity, with a substrate solution containing maleic acid and ammonia and/or ammonium maleate to form L-aspartic acid;

(2) recovering L-aspartic acid from the reaction solution by adding maleic anhydride and/or maleic acid to the reaction solution to crystallize L-aspartic acid; and (3) recycling the mother liquors as the substrate solution by addition of ammonia.

15. L-aspartic acid crystals according to claim 14, wherein ammonia is added to the mother liquors so that an amount of ammonia is from 1.0 to 3.0 mole equivalent relating to maleic acid contained in the mother liquors, and then the mother liquors are recycled as the substrate solution.

16. L-aspartic acid crystals according to claim 14, wherein the mother liquors are recycled as the substrate media after adjusting the pH to 5 to 10.

17. L-aspartic acid crystals according to claim 14, wherein an amount of maleic anhydride, and/or maleic acid added to the reaction solution is from 0.5 to 1.5 mole equivalent relating to an amount of L-aspartic acid present in the reaction solution.

18. L-aspartic acid crystals according to claim 17, wherein an amount of maleic anhydride and/or maleic acid is 1.005 to 1.5 mole equivalent relating to an amount of L-aspartic acid contained in the reaction solution.

19. L-aspartic acid crystals according to claim 1, wherein the maleic anhydride and/or maleic acid are added to the reaction solution at a temperature of 20° to 50° C.

* * * * *